US011197784B2

(12) United States Patent
Blomström et al.

(10) Patent No.: US 11,197,784 B2
(45) Date of Patent: Dec. 14, 2021

(54) ABSORBENT DISPOSABLE ARTICLE COMPRISING A POROUS POLYMER-BASED STRUCTURE

(71) Applicant: Essity Hygiene and Health Aktiebolag, Gothenburg (SE)

(72) Inventors: Philip Blomström, Gothenburg (SE); Peter Rönnberg, Gothenburg (SE); Kent Vartiainen, Gothenburg (SE); Axel Eriksson, Gothenburg (SE); Harald Wutzel, Wien (AU)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 0 days.

(21) Appl. No.: 16/623,616

(22) PCT Filed: Jul. 6, 2017

(86) PCT No.: PCT/EP2017/066937
§ 371 (c)(1),
(2) Date: Dec. 17, 2019

(87) PCT Pub. No.: WO2019/007511
PCT Pub. Date: Jan. 10, 2019

(65) Prior Publication Data
US 2020/0188187 A1 Jun. 18, 2020

(51) Int. Cl.
| | |
|---|---|
| A61F 13/15 | (2006.01) |
| B33Y 10/00 | (2015.01) |
| B33Y 70/00 | (2020.01) |
| B33Y 80/00 | (2015.01) |
| B29C 64/124 | (2017.01) |
| B29C 64/30 | (2017.01) |
| B33Y 40/20 | (2020.01) |
| A61L 15/24 | (2006.01) |
| B29K 105/00 | (2006.01) |
| B29L 31/48 | (2006.01) |

(52) U.S. Cl.
CPC ........ *A61F 13/15642* (2013.01); *A61L 15/24* (2013.01); *B29C 64/124* (2017.08); *B29C 64/30* (2017.08); *B33Y 10/00* (2014.12); *B33Y 40/20* (2020.01); *B33Y 70/00* (2014.12); *B33Y 80/00* (2014.12); *B29K 2105/0064* (2013.01); *B29L 2031/4878* (2013.01)

(58) Field of Classification Search
None
See application file for complete search history.

(56) References Cited

U.S. PATENT DOCUMENTS

| | | | | |
|---|---|---|---|---|
| 2015/0374876 A1* | 12/2015 | Hubbard, Jr. | ...... | B01J 20/28054 502/402 |
| 2016/0175171 A1* | 6/2016 | Brumm | ............ | A61F 13/53708 604/381 |
| 2017/0135869 A1* | 5/2017 | Moriya | ............ | A61F 13/51108 |

FOREIGN PATENT DOCUMENTS

| | | |
|---|---|---|
| EP | 0878481 B1 | 7/2004 |
| EP | 3 162 341 A1 | 5/2017 |
| JP | 2011-000231 A | 1/2011 |
| JP | 2016-013209 A | 1/2016 |
| WO | 9304092 A1 | 3/1993 |
| WO | 9321234 A1 | 10/1993 |

OTHER PUBLICATIONS

International Search Report and Written Opinion for International Application No. PCT/EP2017/066937, dated Dec. 22, 2017, 13 pages.
Owen et al., "Emulsion Templated Scaffolds with Tunable Mechanical Properties for Bone Tissue Engineering", Journal of the Mechanical Behavior of Biomedical Materials, Feb. 2016, 54, 159-172.
Silverstein, M., "Emulsion-templated Porous Polymers: A Retrospective Perspective", Polymer 55 (2014) 304-320.
Office Action (Notice of Reasons for Rejection) dated Apr. 5, 2021, by the Japanese Patent Office in corresponding Japanese Patent Application No. 2019-572214, and an English Translation of the Office Action. (12 pages).

* cited by examiner

*Primary Examiner* — Monica A Huson
*Assistant Examiner* — Kelsey C Grace
(74) *Attorney, Agent, or Firm* — Buchanan Ingersoll & Rooney P.C.

(57) ABSTRACT

An absorbent disposable article, such as a diaper, panty diaper, panty liner, sanitary napkin or incontinence device is disclosed. The article has a porous polymer-based structure obtainable by a process of: (a) depositing and photopolymerizing, layer-by-layer in accordance with a predetermined 3D model, an emulsion having an external continuous phase surrounding droplets of an internal phase having has one or more photopolymerizable monomers and/or oligomers and a photopolymerization initiator; and (b) removing the internal phase from the continuous polymer phase formed from the one or more photopolymerizable monomers and/or oligomers. The process produces a monolithic porous structure having three types of pores: (i) pores resulting from the location from which the internal phase was removed, (ii) pores interconnecting the pores according to (i), and (iii) pores as predetermined by the 3D model. The invention also relates to a method of making the article.

16 Claims, No Drawings

ABSORBENT DISPOSABLE ARTICLE COMPRISING A POROUS POLYMER-BASED STRUCTURE

CROSS REFERENCE TO RELATED APPLICATIONS

This is a U.S. National Phase application of PCT/EP2017/066937, filed Jul. 6, 2017, the disclosure of which is incorporated herein by reference in its entirety for all purposes.

TECHNICAL FIELD

The present invention relates to a hygiene absorbent disposable article such as a diaper or sanitary napkin, comprising a porous polymer-based structure and a process for its manufacture.

BACKGROUND

Polymeric foams for absorbing biofluids are widely used in hygiene absorbent products, such as diapers, incontinence guards (incontinence protection) and sanitary napkins.

In order to obtain good liquid-storage capacity, these polymeric foams are usually open-celled structures. Such structures are commonly prepared by polymerizing high internal phase emulsions (HIPEs).

HIPEs are viscous emulsions in which the major internal phase is dispersed within the continuous, minor external phase. Typically, the internal phase constitutes 74% or more of the volume. When the internal or external (or both) phase contains monomers, polymers can be synthesized within the HIPE. When the monomers are only present in the external phase, porous-emulsion templated polymers can be synthesized.

Once the porous emulsion-templated polymers are synthesized, the internal phase can be removed, leaving a porous structure. Typically, such porous structures have two types of pores: (i) pores resulting from the location from which the internal phase was removed; and (ii) pores interconnecting the pores according to (i).

The prior art discloses polymeric foams having such open-celled structures. The polymeric foams can be made using HIPEs.

More specifically, WO 1993121234 A1 discloses a process for the preparation of a porous crosslinked polymeric material. The process comprises (a) providing a water-in-oil emulsion comprising a mixture of polymerizable monomers and difunctional unsaturated crosslinking monomers, water as the internal phase, and a surfactant and (b) heating the water-in-oil emulsion to polymerize and crosslink the polymerizable monomers. The water-in-oil emulsion can be a HIPE.

WO 1993/04092 A1 discloses a polymeric foam material having a pore volume of from 12 to 100 mL/g; a specific surface area of from 0.5 to 5.0 $m^2/g$; and a resistance to compression deflection such that a confining pressure of 5.1 kPa produces after 15 minutes a strain of from 5 to 95%. These foam materials can be prepared using HIPEs, and are suitable for use in absorbent articles.

EP 0 878 481 B1 discloses a foam material comprising a polymeric foam structure comprising a plurality of cells which are open and essentially in connection with each other when absorption of liquid is initiated. The foam structure comprises a surfactant which is a non-ionic block copolymer, and the internal surfaces of the foam structure are hydrophilic. The foam structures are suitable for use as absorbent articles.

It is one object of the present invention to provide better access to the small pores in foam materials when exposed to bodily fluids.

It is another object of the present invention to provide foam materials for absorbent articles with a good absorbent capacity.

It is a further object in one embodiment of the present invention to control the flow and direction of flow of body liquids in the distribution layers.

Further objects of the present invention will become apparent from the following detailed description thereof.

SUMMARY

The present invention relates to an absorbent disposable article, such as a diaper, panty diaper, panty liner, sanitary napkin or incontinence device, comprising a porous polymer-based structure obtainable by a process comprising the steps of:
  depositing and photopolymerizing, layer-by-layer in accordance with a predetermined 3D model, an emulsion comprising an external continuous phase surrounding droplets of an internal phase, the external phase comprising one or more photopolymerizable monomers and/or oligomers and a photopolymerization initiator, and
  removing the internal phase from the continuous polymer phase formed from the one or more photopolymerizable monomers and/or oligomers
to thereby produce a monolithic porous structure comprising at least the following three types of pores: (i) pores resulting from the location from which the internal phase was removed, (ii) pores interconnecting the pores according to (i) and (iii) pores as predetermined by the 3D model.

In accordance with the usual meaning, "monolithic" means that the porous structure is formed as a single piece.

The present invention also relates to such an absorbent disposable article which comprises a liquid-pervious cover sheet, a backsheet, and an absorbent layer arranged between the cover sheet and the backsheet, the absorbent layer comprising or consisting of the porous polymer-based structure.

The present invention also relates to such an absorbent disposable article which comprises a liquid-pervious cover sheet, a backsheet, an absorbent layer arranged between the cover sheet and the backsheet and a distribution/inlet layer arranged between the cover sheet and the absorbent layer, the distribution/inlet layer comprising or consisting of the porous polymer-based structure.

The present invention also relates to a method of manufacturing an absorbent article comprising the steps of:
  (a) manufacturing a porous polymer-based structure by depositing and photopolymerizing, layer-by-layer in accordance with a predetermined 3D model, an emulsion comprising an external continuous phase surrounding droplets of an internal phase, the external phase comprising one or more photopolymerizable monomers and/or oligomers and a photopolymerization initiator, and
  removing the internal phase from the continuous polymer phase formed from the one or more photopolymerizable monomers and/or oligomers, to thereby produce a monolithic porous structure comprising at least the following three types of pores: (i) pores resulting from the location from which the internal phase was removed, (ii) pores interconnecting the pores according to (i) and (iii) pores as predetermined by the 3D model;
(b) providing a backsheet and a liquid-pervious cover sheet, and assembling the backsheet, the porous polymer-based structure and the liquid-pervious cover sheet to form the absorbent article.

It is believed that the porous polymer-based structure contributes to a good absorbent capacity of the absorbent disposable article. More specifically, the presence of the pores as predetermined by the 3D model (macropores), coupled with the pores resulting from the photopolymerization of the emulsion (micropores), results in a good absorbent capacity. It is believed that the presence of the macropores provides better access to the micropores in foam materials when exposed to body fluids.

Moreover, the micropores do not need to be included in the build file since they are a consequence of the photopolymerization of the emulsion. Thus, the print resolution becomes less important and therefore it is possible to speed-up the printing process.

Another benefit of the present invention is that the absorbent capacity and other relevant parameters of the porous polymer-based structure can be determined in advance with great precision. This is because the size and positioning of the macropores are predetermined, and the size of the micropores can be controlled by adjusting the droplet size of the internal phase of the emulsion.

The following expression "(preferred) embodiment (of the invention)" and similar language should be understood as relating to all aspects thereof, i.e. the claimed method for making an absorbent article and the absorbent article obtainable by the process. The same applies to the description of optional and preferred features.

Where the description refers to "preferred" embodiments/ features, or "embodiments" (also embodiments following terms like "such as" or "e.g."), combinations of these embodiments/features shall also be deemed as disclosed as long as this combination of embodiments/features is technically meaningful.

Hereinafter, the use of the term "comprising" should be understood as disclosing, as a more restricted embodiment, the term "consisting of" as well, as long as this is technically meaningful.

DETAILED DESCRIPTION OF PARTICULAR EMBODIMENTS

The present invention includes the following embodiments ("Items"):

1. An absorbent disposable article, such as a diaper, panty diaper, panty liner, sanitary napkin or incontinence device, comprising a porous polymer-based structure obtainable by a process comprising the steps of
   depositing and photopolymerizing, layer-by-layer in accordance with a predetermined 3D model, an emulsion comprising an external continuous phase surrounding droplets of an internal phase, the external phase comprising one or more photopolymerizable monomers and/or oligomers and a photopolymerization initiator, and
   removing the internal phase from the continuous polymer phase formed from the one or more photopolymerizable monomers and/or oligomers
   to thereby produce a monolithic porous structure comprising at least the following three types of pores: (i) pores resulting from the location from which the internal phase was removed, (ii) pores interconnecting the pores according to (i) and (iii) pores as predetermined by the 3D model.
2. Absorbent disposable article according to item 1, wherein the external continuous phase is an oil phase and the internal phase is an aqueous phase.
3. Absorbent disposable article according to item 1 or 2, wherein the average diameter of the pores according to (ii) is smaller than the average diameter of the pores according to (i) and/or the average diameter of the pores according to (iii) is bigger than the average diameter of the pores according to (i).
4. Absorbent disposable article according to any of items 1, 2 or 3, wherein the average diameter of the pores according to (i) is from 1 to 250 μm, preferably 4 to 150 μm, more preferably 5 to 50 μm, e.g. 5 to 35 μm and/or the average diameter of the pores according to (ii) is from 0.1 to 100 μm, preferably 0.1 to 8 μm, preferably 0.2 to 6 μm, e.g. 0.5 to 5 μm.
5. Absorbent disposable article according to any of items 1, 2, 3 or 4, wherein the average diameter of the pores according to (iii) is from 30 μm to 2000 μm, preferably 50 μm to 1500 μm, e.g. 100 to 1000 μm.
6. Absorbent disposable article according to any of items 1, 2, 3, 4 or 5, wherein the volume ratio of internal phase/external phase is more than 74/26.
7. Absorbent disposable article according to any of items 1, 2, 3, 4, 5 or 6, wherein the one or more photopolymerizable monomers and/or oligomers are selected from (i) glassy monomers such as styrene and styrene-based monomers and isobornyl acrylate and combinations thereof; (ii) rubbery monomers such as (meth)acrylates, (meth)acrylate-based monomers, such as 2-ethylhexylacrylate, butadiene, isoprene and combinations thereof; and (iii) difunctional or higher functional crosslinking monomers such as aromatic divinyl or diallyl monomers, such as divinylbenzene, divinyltoluene, or diallylphtalate, di- or tri(meth)acrylic acid esters of a polyol, such as TMTPA, diethyleneglycol di(meth)acrylate, 3-butylene di(meth)acrylate, and allylmethacrylate, and combinations thereof, and oligomers of these monomers or monomer combinations.
8. Absorbent disposable article according to any of items 1, 2, 3, 4, 5, 6 or 7, wherein the external phase comprises (i) one monomer producing glass-like polymers (high Tg) such as styrene or isobornyl acrylate (IBOA) and (ii) one monomer producing rubber-like polymers (low Tg) such as 2-ethylhexylacrylate (EHA).
9. Absorbent disposable article according to any of items 1, 2, 3, 4, 5, 6, 7 or 8, wherein the absorbent article comprises a liquid-pervious cover sheet, a backsheet, and an absorbent layer arranged between the cover sheet and the backsheet, the absorbent layer comprising or consisting of the porous polymer-based structure.
10. Absorbent disposable article according to item 9, wherein the average diameter of the pores according to (i) is from 1 to 50 μm, preferably 2 to 35 μm, e.g. 4 to 15 μm and/or the average diameter of the pores according to (ii) is from 0.1 to 8 μm, preferably 0.2 to 6 μm, e.g. 0.5 to 5 μm.
11. Absorbent disposable article according to item 9 or 10, wherein the porous polymer-based structure has been subjected to a hydrophilization treatment such as an air plasma treatment, or air plasma treatment followed by the plasma deposition of acrylic acid.

12. Absorbent disposable article according to any of items 9, 10 or 11, wherein the pores according to (iii) comprise SAP particles.
13. Absorbent disposable article according to any of items 1, 2, 3, 4, 5, 6, 7 or 8, wherein absorbent article comprises a liquid-pervious cover sheet, a backsheet, an absorbent layer arranged between the cover sheet and the backsheet and a distribution/inlet layer arranged between the cover sheet and the absorbent layer, the distribution/inlet layer comprising or consisting of the porous polymer-based structure.
14. Absorbent disposable article according to item 13, wherein the average diameter of the pores according to (i) is from 50 to 250 μm, preferably 60 to 200 μm, e.g. 70 to 150 μm and/or the average diameter of the pores according to (ii) is from 0.1 to 100 μm, preferably 0.1 to 8 μm, more preferably 0.2 to 6 μm, e.g. 0.5 to 5 μm.
15. Absorbent disposable article according to item 13 or 14, wherein the porous polymer-based structure has two major opposing sides which are connected by the pores according to (iii) (thereby forming channels) and wherein the pores according to (iii) are arranged such as to direct the flow of body liquids in a lateral direction away from the point of insult.
16. Absorbent disposable article according to any of the preceding items (1, 2, 3, 4, 5, 6, 7, 8, 9, 10, 11, 12, 13, 14 or 15, wherein the total open porosity of the porous polymer-based structure is 60 to 99.5%, preferably 75 to 99%, e.g. 80 to 95%.
17. Method of making an absorbent article according to any items 1, 2, 3, 4, 5, 6, 7, 8, 9, 10, 11, 12, 13, 14, 15 or 16 comprising the steps of
    (a) manufacturing a porous polymer-based structure by depositing and photopolymerizing, layer-by-layer in accordance with a predetermined 3D model, an emulsion comprising an external continuous phase surrounding droplets of an internal phase, the external phase comprising one or more photopolymerizable monomers and/or oligomers and a photopolymerization initiator, and
    removing the internal phase from the continuous polymer phase formed from the one or more photopolymerizable monomers and/or oligomers
    to thereby produce a monolithic porous structure comprising at least the following three types of pores: (i) pores resulting from the location from which the internal phase was removed, (ii) pores interconnecting the pores according to (i) and (iii) pores as predetermined by the 3D model,
    (b) providing a backsheet and a liquid-pervious cover sheet, and assembling the backsheet, the porous polymer-based structure and the liquid-pervious cover sheet to form the absorbent article.
18. Method according to item 17 wherein the step of depositing and photopolymerizing is conducted under UV irradiation, preferably by stereolithography (SLA), digital light processing (DLP) or Continuous Liquid Interface Production (CLIP).

DETAILED DESCRIPTION

The present invention relates to an absorbent disposable article, such as a diaper, panty diaper, panty liner, sanitary napkin or incontinence device, comprising a porous polymer-based structure obtainable by a process comprising the steps of:

depositing and photopolymerizing, layer-by-layer in accordance with a predetermined 3D model, an emulsion comprising an external continuous phase surrounding droplets of an internal phase, the external phase comprising one or more photopolymerizable monomers and/or oligomers and a photopolymerization initiator, and removing the internal phase from the continuous polymer phase formed from the one or more photopolymerizable monomers and/or oligomers to thereby produce a monolithic porous structure comprising at least the following three types of pores: (i) pores resulting from the location from which the internal phase was removed, (ii) pores interconnecting the pores according to (i) and (iii) pores as predetermined by the 3D model.

As "absorbent disposable article" we understand articles capable of absorbing body fluids such as urine, watery faeces, female secretion or menstrual fluids. These absorbent articles include, but are not limited to diapers, panty diapers, panty liners, sanitary napkins or incontinence protection (as for instance used for adults).

In one preferred embodiment, the external continuous phase is an oil phase and the internal phase is an aqueous phase. In another embodiment, the external continuous phase is an aqueous phase and the internal phase is an oil phase.

In one further preferred embodiment, the volume ratio of the internal phase/external phase is more than 74/26. Preferably the volume ratio of the internal phase/external phase is at least 80/20, preferably at least 85/15, preferably at least 90/10 and more preferably at least 95/5. Such volume ratios are characteristic of HIPEs.

Components of External Phase

In one preferred embodiment, the external phase (e.g. the oily external phase) comprises the following components:
  (a) one or more photopolymerizable monomers,
  (b) one or more photopolymerization initiators,
  (c) optionally one or more UV absorbers, and
  (d) optionally one or more solvents.

Preferred amounts of these components, each based on the total weight of the external (oily) phase, are
  (a) at least 50 wt. %, in particular at least 80 wt. %, photopolymerizable monomer/s,
  (b) 0.01 to 10 wt.-%, in particular 0.1 to 5 wt. % photopolymerization initiator,
  (c) optionally 0.01 to 2 wt.-%, in particular 0.05 to 1 wt. % UV absorber,
  (d) not more than 50 wt. %, e.g. 1 to 30 wt. % or 5 to 20 wt. %, solvent/s.

(a) Photopolymerizable Monomer and/or Oligomer

In one preferred embodiment, the one or more photopolymerizable monomers and/or oligomers contained in the external phase are selected from (i) glassy monomers; (ii) rubbery monomers; and (iii) difunctional and higher functional (e.g. trifunctional) crosslinking monomers and/or oligomers of these monomers or monomer combinations.

In the present invention, the term "glassy monomers" refers preferably to monomers which produce an amorphous homopolymer having a glass transition temperature (Tg) of higher than 35° C., preferably 40° C. to 90° C., more preferably 45° C. to 80° C. (high glass transition temperature). Glassy monomers form glass-like polymers.

Glassy monomers are well-established in the art and include styrene, styrene-based monomers (e.g. ethyl styrene), isobornyl acrylate and combinations thereof. Particularly preferred are isobornyl acrylate and styrene.

In the present invention, the term "rubbery monomers" preferably refers to monomers which produce an amorphous homopolymer having a glass transition temperature (Tg) of 35° C. or lower, preferably 30° C. to –30° C., more preferably 25° C. to –20° C., more preferably 20° C. to –15° C. (low glass transition temperature). Rubbery monomers form rubber-like polymers.

Rubbery monomers are well-established in the art and include the C4-C14 alkyl acrylates such as butyl acrylate, hexyl acrylate, octyl acrylate, 2-ethylhexyl acrylate, nonyl acrylate, decyl acrylate, dodecyl (lauryl) acrylate, isodecyl acrylate, and tetradecyl acrylate; aryl and alkaryl acrylates such as benzyl acrylate and nonylphenyl acrylate; the C6-C16 alkyl methacrylates such as hexyl methacrylate, octyl methacrylate, nonyl methacrylate, decyl methacrylate, isodecyl methacrylate, dodecyl (lauryl) methacrylate, and tetradecyl methacrylate; acrylamides such as N-octadecyl acrylamide; C4-C12 alkyl styrenes such as p-n-octylstyrene; isoprene; butadiene; and combinations of such monomers. Particularly preferred is 2-ethylhexylacrylate.

The glass transition temperature (Tg) is defined as the temperature at which a polymer changes from hard and brittle to soft and pliable. That is, Tg represents the midpoint of the transition between the glassy and rubbery states of the polymer. Tg can be measured by Differential Scanning Calorimetry according to ASTM D7426-08(2013).

Without wishing to be bound by theory, it is believed that the glassy monomers impart sufficient rigidity to the porous polymer-based structure, and that the rubbery monomers impart sufficient flexibility to the porous polymer-based structure so that it is suitable for its desired function.

Difunctional and higher functional (e.g. trifunctional) crosslinking monomers are well-established in the art and examples include diurethane dimethacrylate (DUDMA); aromatic divinyl monomers such as divinylbenzenes and analogues thereof such as divinyltoluenes, divinylxylenes, divinylnaphthalenes, divinylalkylbenzenes, divinylphenanthrenes, divinylbiphenyls, divinyldiphenylmethanes, divinylbenzyls, divinylphenylethers, divinyldiphenylsulfides, divinylfurans, divinylsulfide, divinylsulfone, and mixtures thereof; diacrylates of diols and analogs thereof such as dimethacrylates, diacrylamides and dimethacrylamides; diallyl monomers such as diallylphtalate; di(meth)acrylic acid esters of a polyol, such as diethyleneglycol di(meth)acrylate, 3-butylene di(meth)acrylate and allylmethacrylate; trimethylolpropane triacrylate (TMPTA); and poly(propylene glycol) dimethacrylate (PPGDMA) and combinations thereof. Particularly preferred are aromatic divinyl monomers such as divinylbenzenes and analogues thereof such as divinyltoluenes, divinylxylenes, divinylnaphthalenes, divinylalkylbenzenes, divinylphenanthrenes, divinylbiphenyls, divinyldiphenylmethanes, divinylbenzyls, divinylphenylethers, divinyldiphenylsulfides, divinylfurans, divinylsulfide, divinylsulfone, and mixtures thereof; and TMPTA.

In another preferred embodiment, the external phase comprises (i) one monomer producing glass-like polymers and (ii) one monomer producing rubber-like polymers. Suitable monomers are the same as listed above. Particularly preferred combinations are 2-ethylhexylacrylate/styrene and 2-ethylhexylacrylate/isobornyl acrylate. In this embodiment the aforementioned difunctional and higher functional monomer (iii) such as TMTPA, PPGDMA or DUDMA may also be added.

It is generally preferred to use a weight ratio (i/ii) of glassy monomer/oligomer (i) to rubbery monomer/oligomer (ii) of 5/95 to 60/40, preferably 10/90 to 50/50, e.g. 15/85 to 40/60.

The difunctional and higher functional (e.g. trifunctional) crosslinking monomer/oligomer (iii) can be used alone but also in mixtures with glassy monomer/oligomer (i) and/or rubbery monomer/oligomer (ii). In the latter case, the amount of (iii) is preferably 1 to 40 wt. %, more preferably 5 to 30 wt. %, e.g. 10 to 25 wt. %, based on the total amount of monomers and/or oligomers (i), (ii) and (iii).

Further, in order to increase the flexibility of porous polymer-based structure a multifunctional thiol such as pentaerythritol tetrakis 3-mercaptopropionate ("TT") may be added to the emulsion, as taught by Susec in Macromol. Rapid Commun. 2013, 34, 938-943.

(b) Photoinitiator

The present invention utilises a photopolymerization initiator ("photoinitiator") in the external phase to initiate the polymerization of the monomers to form a polymer. Suitable photoinitiators that may be used in an external oily phase include acyl phosphine oxides such as bis-acylphosphine oxide (BAPO), diphenyl(2,4,6-trimethylbenzoyl)-phosphine oxide (e.g. Irgacure 819), and (2,4,6-trimethylbenzoyl)-phosphine oxide; or α-hydroxy, α-alkoxy or α-aminoarylketones such as 2-hydroxy-2-methylpropiophenone; which may also be used in combination as in (2,4,6-trimethylbenzoyl)-phosphine oxide/2-hydroxy-2-methylpropiophenone (e.g. in a 50/50 volume ratio); and cleavable germanium-based initiators such as Ivocerin. The use of a photoiniator can lead to a more homogeneous structure than the thermoinitiators used for the manufacture of known HIPE-based polymer-based absorbent structures.

(c) UV Absorber (Optional)

In one preferred embodiment, the photopolymerizable composition may further comprise one or more (c) UV absorbers. The type of UV absorber is in principle not limited as long as it is capable of absorbing UV light, is soluble in the photopolymerizable composition and preferably shows low volatility. If UV light is used as light source in the photopolymerization step, it can be beneficial to use an UV absorber since the same reduces the penetration depth of the UV light rays. This prevents the photopolymerizable monomers and/or oligomers from starting to photopolymerize in areas in vicinity to the actual layer to be produced and thereby enhances the resolution of the structural features of the monolithic absorbent structure.

The UV absorber may be used singly or in combination. The UV absorber may be an organic or an inorganic compound. Typical commercially available examples of organic UV-absorber are benzotriazoles such as 2-(2'-Hydroxy-5'-methylphenyl)benzotriazole, 2-(2'-Hydroxy-3'-tert-butyl-5'-methylphenyl)-5-chlorobenzotriazole, 2-(2'-Hydroxy-3',5'-di-tert-amylphenyl)benzotriazole, 2-(2'-Hydroxy-5'-tert-octylphenyl)benzotriazole, 2,2'-Methylenebis[6-(2H-benzotriazol-2-yl)-4-tert-octylphenol], 6-(2-benzotriazolyl)-4-tert-octyl-6'-tert-butyl-4'-methyl-2,2'-methylenebisphenol such as Tinuvin Carboprotect® produced by BASF.

The content of the UV absorber in the external continuous phase is usually up to 2 wt. %, based on the weight of the external continuous phase, e.g. 0.01 to 2 weight percent, preferably 0.05 to 1 weight percent.

(d) Solvent (Optional)

Further, as mentioned before, a solvent/s such as toluene may be added to the external continuous phase in order to adjust the viscosity of the emulsion and/or pore structure of the final porous polymer-based structure. Then it may become necessary to remove residual solvent in a separate method step, for instance by washing with a volatile solvent and/or evaporation (e.g. under vacuum).

Aqueous Internal Phase

In one embodiment, the internal phase is water. In one embodiment, the internal phase comprises a metal salt, preferably an alkali earth metal salt, more preferably calcium chloride. The content of the metal salt is preferably 0.1-20 wt. %, more preferably 1 to 10 wt. %, more preferably about 5 wt. %. The presence of the metal salt can prevent, or at least reduce, Ostwald ripening.

In one embodiment, a surfactant may be included in the emulsion to permit the formation of a stable emulsion. Suitable surfactants include sorbitan esters such as sorbitan laurates (e.g., SPAN™ 20), sorbitan palmitates (e.g., SPAN™ 40), sorbitan stearates (e.g., SPAN™ 60 and SPAN™ 65), sorbitan monooleates (e.g., SPAN™ 80), sorbitan trioleates (e.g., SPAN™ 85), sorbitan sesquioleates (e.g., EMSORB™ 2502), and sorbitan isostearates (e.g., CRILL™ 6); polyglycerol esters and ethers (e.g., TRIODAN™ 20); polyoxyethylene fatty acids, esters and ethers such as polyoxyethylene (2) oleyl ethers, polyethoxylated oleyl alcohols (e.g. BRIJ™ 92 and SIMUSOL™ 92), etc.; mono-, di-, and triphosphoric esters such as mono-, di-, and triphosphoric esters of oleic acid (e.g., HOSTAPHAT); polyoxyethylene sorbitol esters such as polyoxyethylene sorbitol hexastearates (e.g., ATLAS™ G-1050); ethylene glycol fatty acid esters; glycerol mono-isostearates (e.g., IMWITOR 780K); ethers of glycerol and fatty alcohols (e.g., CREMOPHOR WO/A); esters of polyalcohols; synthetic primary alcohol ethylene oxide condensates (e.g., SYNPERONIC A2); mono and diglycerides of fatty acids (e.g., ATMOS™ 300); triblock copolymer of poly(propylene oxide) and poly(ethylene oxide) (e.g. PEL121); PEG 30-di-polyhydroxystearic acid (e.g. Hypermer B246); and polyglycerol polyricinoleate. Preferred surfactants include PEL121, Hypermer B246, polyglycerol polyricinoleate, sorbitan stearates (e.g. SPAN 65), sorbitan monooleates (e.g., SPAN™ 80) and sorbitan trioleates (e.g., SPAN™ 85), and particularly preferred are sorbitan monooleates (e.g., SPAN™ 80) and sorbitan trioleates (e.g., SPAN™ 85). The surfactant is preferably used in an amount of 1 to 40 wt. %, in particular 2 to 35 wt. %, e.g. 3 to 25 wt. % or 3 to 15 wt. %, each based on the weight of the external continuous phase.

Pore Diameters

In accordance with the present invention, there are no specific limitations as to the diameter of the pores. Suitable diameters can be selected by a person skilled in the art having regard to known criteria such as mechanical stability, capillary forces, a sufficiently high absorption speed, etc. The pore diameter refers to the average pore diameter since pores in a given sample will not necessarily be of approximately the same size.

In one preferred embodiment, the average diameter of the pores according to (ii) is smaller than the average diameter of the pores according to (i) and/or the average diameter of the pores according to (iii) is bigger than the average diameter of the pores according to (i).

In one further preferred embodiment, the average diameter of the pores according to (i) is from 1 to 250 μm, preferably 4 to 150 μm, more preferably 5 to 50 μm, e.g. 5 to 35 μm and/or the average diameter of the pores according to (ii) is from 0.1 to 100 μm, preferably 0.1 to 8 μm, more preferably 0.2 to 6 μm, e.g. 0.5 to 5 μm.

The diameter of pore type (i) depends upon the size of the internal phase droplets prior to polymerization. The larger the internal phase droplet size, the larger the diameter of pore type (i). Methods for altering the internal phase droplet size are well known in the art and include changing the energy input by mixing/shearing, adjusting the temperature, adding solvents, aging of the emulsion and changing surfactant composition and amount. There are other methods in which the droplet size can be altered, and the skilled person would be aware of such methods.

The diameter of pore type (ii) increases with increasing internal phase volume.

A number of methods are available for determining the average pore diameter in porous polymer-based structures. One useful method for determining the average pore diameter involves direct photographic measurement, e.g. by SEM. In this method, a photomicrograph of a fracture surface of the porous polymer-based structure is made. Superimposed on this photomicrograph is a scale representing a dimension of e.g. 10 microns. Such a scale can be used to determine the average pore diameter via an image analysis procedure. Direct photographic measurement is used herein to measure the average pore diameter.

The average diameter of the pores can also be determined by a method described by Susec in Macromol. Rapid Commun. 2013, 34, 938-9438 (item 3.5).

In one preferred embodiment, the average diameter of the pores according to (iii) is from 30 μm to 2000 μm, preferably 50 μm to 1500 μm, e.g. 100 to 1000 μm. The diameter of pore type (iii) is predetermined by the 3D model, and hence can be easily controlled and measured.

Aqueous Phase as External Continuous Phase

According to one embodiment, the external continuous phase is an aqueous phase as described before and the internal phase is an oil phase. The monomer is preferably selected from acrylamide, hydroxyethyl acrylate (HEA), 2-hydroxyethyl methacrylate (HEMA) and N-isopropyl acrylamide. The monomer content is preferably around 20 to 40%, more preferably 25 to 35%, more preferably about 30% of the aqueous external phase. A preferred crosslinking agent is N,N-methylenebisacrylamide, since this increases the specific surface area of the polymer which results in increased water absorption.

Suitable photoinitiators that may be used in an external aqueous phase include water-soluble peroxo compounds such as potassium peroxodisulfate (PPS) and hydrogen peroxide.

Suitable emulsions for hydrophilic polyHIPEs and manufacturing conditions have also been described by Silverstein (Polymer 55 (2014) 304-320).

Absorbent Article and Absorbent Layer Comprising the Porous Polymer-Based Structure In one preferred embodiment, the absorbent article comprises a liquid-pervious cover sheet, a backsheet, and an absorbent layer arranged between the cover sheet and the backsheet, the absorbent layer comprising or consisting of the porous polymer-based structure.

A liquid-pervious coversheet (topsheet) faces the wearer's body. On the opposite side of the absorbent article a coversheet (backsheet) may present, which during use is normally facing the wearer's garment and is preferably liquid-impervious. The backsheet can for instance comprise or consist of a plastic film, a plastic-coated nonwoven or a hydrophobic nonwoven.

A suitable topsheet may be manufactured from a wide range of materials such as woven and nonwoven materials (e.g. a nonwoven web of fibers), polymeric materials such as apertured plastic films, e.g. apertured-formed thermoplastic films and hydroformed thermoplastic films; porous foams;

reticulated foams; reticulated thermoplastic films; and thermoplastic scrims. Suitable woven and nonwoven materials can be comprised of natural fibers or from a combination of natural and synthetic fibers. Examples of suitable synthetic fibers which may comprise all or part of the topsheet include but are not limited to polyamide (e.g. nylon), acrylic (e.g. polyacrylonitrile), aromatic polyamide (e.g. aramide), polyolefin (e.g. polyethylene and polypropylene), polyester, butadiene-styrene block copolymers, natural rubber, latex, spandex (polyurethane) and combinations thereof. Synthetic fibers that contain more than one type of repeat unit can result from combining repeat units at the molecular level within each macromolecular strand (copolymer), between macromolecular strands (homopolymer blends), or combinations thereof (copolymer blends); or they can result from combining repeat units at a higher scale level with distinct nanoscopic, microscopic, or macroscopic phases (e.g., multicomponent fibers). Each component of a multicomponent fiber can comprise a homopolymer, a copolymer, or blends thereof. Bicomponent fibers are common versions of multicomponent fibers. The two or more types of repeat units in a copolymer can be arranged randomly or in alternating blocks of each type. Blocks of different types of repeat units can be jointed to one another at their respective ends (block copolymers) or between the respective end of at least one block (graft copolymers).

Nonwoven materials can be formed by direct extrusion processes during which the fibers and the nonwoven materials are formed at about the same point in time, or by preformed fibers which can be laid into nonwoven materials at a distinctly subsequent point in time. Exemplary direct extrusion processes include but are not limited to: spunbonding, meltblowing, solvent spinning, electrospinning and combinations thereof typically forming layers. Exemplary "laying" processes including wet laying and dry laying. Exemplary dry laying processes include but are not limited to air laying, carding and combinations thereof typically forming layers. Combinations of the above processes yield nonwovens commonly called hybrides or composites. The fibers in a nonwoven material are typically joined to one or more adjacent fibers at some of the overlapping junctions. Fibers can be joined by mechanical entanglement, by chemical bond or by combinations thereof.

The backsheet prevents the exudates absorbed by the absorbent layer from soiling other external articles that may contact the absorbent article, such as bed sheets and undergarments. In preferred embodiments, the backsheet is substantially impervious to liquids (e.g., urine) and comprises a laminate of a nonwoven and a thin plastic film such as a thermoplastic film having a thickness of about 0.012 mm to about 0.051 mm. Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the absorbent article while still preventing exudates from passing through the backsheet. Exemplary breathable materials may include materials such as woven webs, nonwoven webs, composite materials such as film-coated nonwoven webs, and microporous films.

In a preferred aspect of this embodiment, the average diameter of the pores according to (i) is from 1 to 50 µm, preferably 2 to 35 µm, e.g. 4 to 15 µm and/or the average diameter of the pores according to (ii) is from 0.1 to 8 µm, preferably 0.2 to 6 µm, e.g. 0.5 to 5 µm.

In another preferred aspect of this embodiment, the porous polymer-based structure has been subjected to a hydrophilization treatment such as an air plasma treatment, or air plasma treatment followed by the plasma deposition of acrylic acid. Suitable plasma treatment methods are disclosed in Owen et al., Journal of the Mechanical Behavior of Biomedical Materials, 2016 February, 54, 159-172.

In another preferred aspect of this embodiment, the pores according to (iii) comprise superabsorbent polymer (SAP) particles.

There are a number of possible ways to insert SAP particles into the porous polymer-based structure. These include the following methods:

- The 3D printed object is dipped in a vat filled with SAP powder while still on the build plate. The SAP powder is sucked up through the structure. The SAP powder gets trapped in cavities within the structure. The cavities are designed and positioned so that the right amount of SAP powder ends up in the right place.
- The 3D-printed structure is lowered into a fluidized bed of SAP particles. The particles flow into cavities within the structure. The fluidization is turned off. The remaining SAP powder within the structure gets stuck inside the cavities/pores in the 3D printed structure.
- The 3D printed structure is lowered into a vat filled with SAP particles. The wetness of the residual monomers on the surface of the 3D printed detail works as glue, which allows for the SAP powder to adhere to the object. Subsequently, the detailed is post cured in a UV chamber.
- SAP powder is deposited into the 3D printed structure from holes in the build plate.
- A nozzle sprays a UV curable SAP coating onto the 3D printed object. The coating is subsequently cured in a UV chamber.
- The 3D printed structure is lowered into a vat filled with SAP particles. The object and/or the SAP particles get charged. The electric charge makes the particles adhere to the structure by means of static current.
- SAP is extruded/injected into the structure using multiple needles.
- The build plate is lowered into a vat filled with SAP particles. The build plate starts to vibrate causing the SAP particles to get caught in the pores in the structure.

Distribution/Inlet Layer Comprising the Porous Polymer-Based Structure

In one preferred embodiment, the absorbent article comprises a liquid-pervious cover sheet, a backsheet, an absorbent layer arranged between the cover sheet and the backsheet and a distribution/inlet layer arranged between the cover sheet and the absorbent layer, the distribution/inlet layer comprising or consisting of the porous polymer-based structure. The acquisition/distribution layers aid in removing body liquids penetrating the topsheet and/or distributing the incoming body liquids over the entire surface of the absorbent layer.

In this embodiment, the absorbent layer may comprise any absorbent material that is generally compressible, conformable, non-irritating to the wearer's skin and capable of absorbing and retaining liquids such as urine and other body exudates. The absorbent layer may be partially or totally surrounded by a core wrap. In some specific products it may also be totally omitted.

The topsheet and backsheet may be selected from the same materials as described before.

In a preferred aspect of this embodiment, the average diameter of the pores according to (i) is from 50 to 250 µm, preferably 60 to 200 µm, e.g. 70 to 150 µm and/or the average diameter of the pores according to (ii) is from 0.1 to 100 µm, preferably 0.1 to 8 µm, more preferably 0.2 to 6 µm, e.g. 0.5 to 5 µm.

When designing absorbent articles it is often one aim to make the best possible use of the available absorbent capacity. In one preferred embodiment of the invention, the porous polymer-based structure has two major opposing sides which are connected by the pores according to (iii) (thereby forming channels) and wherein the pores according to (iii) are arranged such as to direct the flow of body liquids in a lateral direction away from the point of insult.

Porosity

It is one further benefit of the present invention that, by using an appropriate 3D model, the total open porosity can be easily determined prior to the manufacture of the porous polymer-based structure. In one preferred embodiment, the total open porosity of the porous polymer-based structure is 60 to 99.5%, preferably 75 to 99%, more preferably 80 to 95%.

The total open porosity is measurable by intrusion methods, e.g. mercury intrusion, which is a well-known method in the art; see e.g. the mercury porosimetry method described by Johnson (Adv. Mater. 2013, 25, 3178-3181).

Method of Manufacturing an Absorbent Article

The present invention also relates to a method of making an absorbent article, the method comprising the steps of:

(a) manufacturing a porous polymer-based structure by depositing and photopolymerizing, layer-by-layer in accordance with a predetermined 3D model, an emulsion comprising an external continuous phase surrounding droplets of an internal phase, the external phase comprising one or more photopolymerizable monomers and/or oligomers and a photopolymerization initiator, and removing the internal phase from the continuous polymer phase formed from the one or more photopolymerizable monomers and/or oligomers, to thereby produce a monolithic porous structure comprising at least the following three types of pores: (i) pores resulting from the location from which the internal phase was removed, (ii) pores interconnecting the pores according to (i) and (iii) pores as predetermined by the 3D model; and (b) providing a backsheet and a liquid-pervious cover sheet, and assembling the backsheet, the porous polymer-based structure and the liquid-pervious cover sheet to form the absorbent article.

The size of the droplets in the emulsion (e.g. HIPE emulsion) prior to polymerisation largely governs the size of the first level of pores (i) within the porous polymer-based structure (e.g. HIPE material). There are different factors influencing the droplet size in the porous polymer-based structure (e.g. HIPE material) and methods for tuning include changing the energy input by mixing/shearing, adjusting the temperature, adding solvents, aging of the emulsion, and changing the surfactant composition and amount, as described by Susec in Macromol. Rapid Commun. 2013, 34, 938-943. Depending on the use of cross-linking monomers and porogenic solvent a fourth level of meso or micropores can be introduced within the polymer phase.

According to one further preferred embodiment of the invention, the step of depositing and photopolymerizing is conducted under UV irradiation, preferably by stereolithography (SLA), digital light processing (DLP), or continuous liquid interphase production (CLIP).

All three techniques are known 3D printing techniques utilizing the layer-by-layer photopolymerization of a photopolymerizable composition.

Stereolithography (SLA also known as stereolithography apparatus, optical fabrication, photo solidification, or resin printing) is a form of 3D printing technology used for creating models, prototypes, patterns, and production parts in a layer-by-layer fashion using photopolymerization. Those polymers then make up the body of a three-dimensional solid. Stereolithography is an additive manufacturing process that works by focusing an ultraviolet (UV) laser on to a vat of photopolymer resin. With the help of computer-aided manufacturing or computer-aided design software (CAM/CAD), the UV laser is used to draw a pre-programmed design or shape onto the surface of the photopolymer vat. Because photopolymers are photosensitive under ultraviolet light, the resin is solidified and forms a single layer of the desired 3D object. This process is repeated for each layer of the design until the 3D object is complete.

Digital Light Processing (DLP) is a similar process to stereolithography (SLA) in that it is a 3D printing process that works with photopolymers. The major difference is the light source. DLP uses a more conventional light source, such as an arc lamp, with a liquid crystal display panel or a deformable mirror device (DMD), which is applied to the entire surface of the vat of photopolymer resin in a single pass, generally making it faster than SLA. Also like SLA, DLP produces highly accurate parts with excellent resolution. One advantage of DLP over SLA is that only a shallow vat of resin is required to facilitate the process, which generally results in less waste and lower running costs. If used with a supporting structure, any geometry is possible. This technology is also available for the personal printer sector, and it is appealing due to its relatively low investment costs.

Currently, the best resolution DLP machines on the market print in a resolution of approx. 16×16 µm in the X/Y-plane and 10 µm in the Z-direction.

The resolution of DLP is sufficient to form microporous structures with pores small enough to achieve a porous polymer-based structure making use of capillary forces.

DLP is one of the fastest 3D printing methods available. The DLP projector displays an image, depicting a cross section of a 3D part onto the surface of the resin. The exposed resin solidifies to a predetermined thickness forming one layer, hence each layer prints instantly, regardless of the object's size measured in the X/Y-plane or the object's geometrical complexity.

The main factor that limits the speed of DLP printing is that the build plate needs to be lifted and repositioned before a new layer can be printed. There are two reasons why the object must be lifted before a new layer can be printed:

(1) The object is lifted from the bottom surface of the resin vat in order to allow for new resin to flow in between the previous layer and the surface on which the layer/image is projected.

(2) The printed layer must be detached/peeled off from the bottom surface of the resin vat before a new layer can be printed.

In order to speed up the DLP printing process Carbon 3D has invented a DLP printer which can print continuously without repositioning the building plate between each layer. Carbon 3D's invention is called CLIP, Continuous Liquid Interface Production.

Continuous Liquid Interface Production (CLIP; originally Continuous Liquid Interphase Printing) is a method of 3D printing that uses photopolymerization to create solid objects of a wide variety of shapes using resins. It was invented by Joseph DeSimone, Alexander and Nikita Ermoshkin and Edward T. Samulski and was originally owned by EiPi Systems, but is now being developed by Carbon 3D. The continuous process begins with a pool of liquid photopolymer resin. Part of the pool bottom is transparent to ultraviolet light (the "window"). An ultraviolet light beam shines through the window, illuminating the precise cross-section of the object. The light causes the resin to solidify. The object rises slowly enough to allow resin to flow under and maintain contact with the bottom of the object. An oxygen-permeable membrane lies below the resin, which creates a "dead zone" (persistent liquid interface) preventing the resin from attaching to the window (photopolymerization is inhibited between the window and the polymerizer). Unlike stereolithography, the printing process is continuous.

Carbon 3D has replaced the window in the bottom of the resin vat with a special window that is transparent to light and permeable to oxygen. The oxygen acts as a counterbalance to the UV light, hence preventing the hardening of the photopolymer. By controlling the oxygen flux through the window, CLIP creates a thin layer of uncured resin between the window and the object (referred to as "dead-zone" by Carbon 3D). The uncured layer eliminates the need for repositioning the build plate since the printed object is never in direct contact with the window in the bottom of the resin vat.

Below examples of layerless/continuous DLP printers are given which can be used in the present invention:
  Layerless/continuous DLP printer developed by students at University of Buffalo: Krassenstein, E. (2015) Student creates super-fast 'membrane-based' 3D printer—prints 40×40×100 mm objects at 10 microns in 12 minutes. Available at: http://3dprint.com54864/super-fast-3d-printer/. (Krassenstein, 2015)
  Layerless/continuous DLP printer developed by Gizmo 3D: Gizmo 3D printers DLP 3D Printe (no date) Available at: http://www.gizmo3dprinters.com.au.
  Layerless/continuous DLP printer developed by Carima: Carima (no date) Available at: http://www.carima.com.
  Layerless/continuous DLP printer developed by NewPro 3D: D, N. 3 (2016b) Newpro3D super-fast 3D printer, world's fastest 3D printer of the day. Available at: http://newpro3d.comfili-technology/
  Layerless/continuous DLP printer developed by Nexa3D: Smart (no date) Available at: http://www.nexa3d.com In one embodiment of the invention, any residual monomer and/or oligomer and/or the internal phase are removed using any of the following methods:
  The build plate is moved to a perforated plate where residual monomer(s) and/or oligomer(s) and the internal phase are sucked out from the structure. The residual material is filtered and reused. The structure is then irradiated with light (e.g. UV) in order to cure any residual monomer(s) and/or oligomer(s) stuck on the surface of the structure. The structure is then dried (e.g. using heat and/or microwaves).
  The build plate is moved to a closed chamber. The building plate rotates within the chamber in order to centrifuge out the uncured monomer(s) and/or oligomer(s) and the internal phase. The structure is then irradiated with light (e.g. UV) in order to cure any residual monomer(s) and/or oligomer(s) stuck on the surface of the structure. The structure is then dried (e.g. using heat and/or microwaves).
  The build plate is moved to a perforated plate. The build plate presses the geometry onto the perforated plate in order to squeeze out uncured monomer(s) and/or oligomer(s) and the internal phase. The structure is then irradiated with light (e.g. UV) in order to cure any residual monomer(s) and/or oligomer(s) stuck on the surface of the structure. The structure is then dried (e.g. using heat and/or microwaves).
  The residual monomer(s) and/or oligomer(s) and the internal phase are squeezed out from the structure using rollers. The structure is then irradiated with light (e.g. UV) in order to cure any residual monomer(s) and/or oligomer(s) stuck on the surface of the structure. The structure is then dried (e.g. using heat and/or microwaves).

The internal phase can be removed from the structure using vacuum optionally in combination with pressure, microwaves and/or heat.

In one embodiment of the present invention, a process for producing a structure having inlet/distribution layers is described:
  one or multiple layers having inlet properties are printed using a first emulsion.
  the residual resin and the aqueous phase are removed using one of the above-mentioned methods.
  the resin vat is emptied and filled with a new resin or replaced by a new resin vat.
  one or multiple layers having distribution properties are printed using a second emulsion.
  the residual resin and the aqueous phase are removed using one of the above-mentioned methods.
  the resulting structure is dried using heat, pressure and/or microwaves in order to fully remove the aqueous phase.
  the resulting structure is irradiated with UV light in order to cure any residual monomer(s) and/or oligomer(s) stuck on the surface of the structure.
  SAP is inserted into the structure using on the above-mentioned methods.

Layer-by-layer assembly methods can sometimes be sensitive to the viscosity of the emulsion used. For example, SLA generally requires the emulsion to have a low viscosity. At lower viscosity, print failure can occur due to line spreading. With decreased line height, the distance between the nozzle and printing layer becomes too large to accurately deposit extruded material. Accordingly, in one embodiment, toluene is added to an oily external phase to lower the viscosity. The addition of toluene enables successful printing if the emulsion is too viscous to print effectively. Moreover, the addition of toluene has no detrimental effect on the porous polymer-based structure. Preferably, 10 to 50 vol % with regards to monomers of toluene is added.

In one typical embodiment of step (a) the emulsion is prepared as follows. Suitable amounts of monomer/oligomer selected from (i), (ii) and (iii) are mixed followed by the addition of surfactant. The mixture is allowed to dissolve. The resulting solution is protected against light exposure and agitated while adding photoinitiator. Then, under continued stirring, the aqueous phase, for instance water, is added drop-wise until an emulsion with a suitable viscosity has formed. Subsequently, the LBL-photopolymerisation step is conducted with a suitable UV curing system. The resulting monolithic porous polymer-based structure is then recovered, and the aqueous phase removed, for instance by immersion in a volatile solvent such as acetone and/or drying (e.g. under vacuum).

The porous polymer-based structure of the invention can be manufactured in a manner similar to that described by Sears (Macromol. Rapid Commun. 2016, DOI: 10.1002/marc.201600236), Susec (Macromol. Rapid Commun. 2013, 34, 938-943), Owen (Journal of the Mechanical Behavior of Biomedical Materials, 2016 February, 54, 159-172), Johnson (Adv. Mater. 2013, 25, 3178-3181) and Silverstein (Polymer 55 (2014) 304-320).

Depending on the intended function, it may be desirable to render the porous polymer-based structures more flexible by increasing the ratio of rubbery monomers to glassy monomers. Rubbery monomers yield polymers with lower Tg values, and hence the resulting structure is more flexible.

In order to improve the wettability of the porous polymer-based structures (e.g. polyHIPE structures) techniques described by Owen can be used also in the present invention. These include pcAir or pdAAc plasma treatment which is based on the addition of negatively charged carboxyl groups (pdAAc) or the deposition of oxygen-containing groups (pcAir).

The invention claimed is:

1. An absorbent disposable article, comprising a porous, open-celled polymer-based structure obtainable by a process comprising the steps of
   depositing and photopolymerizing, layer-by-layer in accordance with a predetermined 3D model, an emulsion comprising an external continuous phase surrounding droplets of an internal phase, the external phase comprising one or more photopolymerizable monomers and/or oligomers and a photopolymerization initiator, and
   removing the internal phase from the continuous polymer phase formed from the one or more photopolymerizable monomers and/or oligomers
   to thereby produce a monolithic porous, open-celled structure comprising at least the following three types of pore: (i) pores resulting from the location from which the internal phase was removed, (ii) pores interconnecting the pores according to (i), and (iii) pores as predetermined by the 3D model.

2. The absorbent disposable article according to claim 1, wherein the external continuous phase is an oil phase and the internal phase is an aqueous phase.

3. The absorbent disposable article according to claim 1, wherein the average diameter of the pores according to (ii) is smaller than the average diameter of the pores according to (i) and/or the average diameter of the pores according to (iii) is bigger than the average diameter of the pores according to (i).

4. The absorbent disposable article according to claim 1, wherein the average diameter of the pores according to (i) is from 1 to 250 µm, and/or the average diameter of the pores according to (ii) is from 0.1 to 100 µm.

5. The absorbent disposable article according to claim 1, wherein the average diameter of the pores according to (iii) is from 30 µm to 2000 µm.

6. The absorbent disposable article according to claim 1, wherein the volume ratio of internal phase/external phase is more than 74/26.

7. The absorbent disposable article according to claim 1, wherein the one or more photopolymerizable monomers and/or oligomers are selected from (i) glassy monomers; (ii) rubbery monomers; and (iii) difunctional or higher functional crosslinking monomers.

8. The absorbent disposable article according to claim 1, wherein the external phase comprises (i) one monomer producing glass-like polymers (high Tg) and (ii) one monomer producing rubber-like polymers (low Tg).

9. The absorbent disposable article according to claim 1, wherein the absorbent article comprises a liquid-pervious cover sheet, a backsheet, and an absorbent layer arranged between the cover sheet and the backsheet, the absorbent layer comprising or consisting of the porous polymer-based structure.

10. The absorbent disposable article according to claim 9, wherein the average diameter of the pores according to (i) is from 1 to 50 µm and/or the average diameter of the pores according to (ii) is from 0.1 to 8 µm.

11. The absorbent disposable article according to claim 9, wherein the porous polymer-based structure has been subjected to a hydrophilization treatment.

12. The absorbent disposable article according to claim 9, wherein the pores according to (iii) comprise SAP particles.

13. The absorbent disposable article according to claim 1, wherein absorbent article comprises a liquid-pervious cover sheet, a backsheet, an absorbent layer arranged between the cover sheet and the backsheet and a distribution/inlet layer arranged between the cover sheet and the absorbent layer, the distribution/inlet layer comprising or consisting of the porous polymer-based structure.

14. The absorbent disposable article according to claim 13, wherein the average diameter of the pores according to (i) is from 50 to 250 µm and/or the average diameter of the pores according to (ii) is from 0.1 to 100 µm.

15. The absorbent disposable article according to claim 13, wherein the porous polymer-based structure has two major opposing sides which are connected by the pores according to (iii) (thereby forming channels) and wherein the pores according to (iii) are arranged to direct the flow of body liquids in a lateral direction away from the point of insult.

16. The absorbent disposable article according to claim 1, wherein the total open porosity of the porous polymer-based structure is 60 to 99.5%.

* * * * *